United States Patent
McSurdy, Jr.

(10) Patent No.: US 7,192,273 B2
(45) Date of Patent: Mar. 20, 2007

(54) SYSTEM AND METHOD FOR PALATAL EXPANSION

(76) Inventor: David W. McSurdy, Jr., 128 Mennonite Rd., Collegeville, PA (US) 19426

( * ) Notice: Subject to any disclaimer, the term of this patent is extended or adjusted under 35 U.S.C. 154(b) by 233 days.

(21) Appl. No.: 10/636,313

(22) Filed: Aug. 7, 2003

(65) Prior Publication Data

US 2005/0032015 A1 Feb. 10, 2005

(51) Int. Cl.
*A61C 3/00* (2006.01)
(52) U.S. Cl. .............................. 433/6; 433/24
(58) Field of Classification Search ............ 433/6, 433/7, 24
See application file for complete search history.

(56) References Cited

U.S. PATENT DOCUMENTS

| | | | |
|---|---|---|---|
| 4,609,349 A | * | 9/1986 | Cain ............... 433/6 |
| 4,886,451 A | | 12/1989 | Cetlin |
| 5,037,295 A | * | 8/1991 | Bergersen ............ 433/6 |
| 5,242,304 A | * | 9/1993 | Truax et al. ......... 433/177 |
| 5,816,800 A | | 10/1998 | Brehm et al. |
| 5,904,479 A | | 5/1999 | Staples |
| 5,975,893 A | | 11/1999 | Chishti et al. |
| 6,398,548 B1 | | 6/2002 | Muhammad et al. |
| 6,402,510 B1 | | 6/2002 | Williams |
| 6,520,772 B2 | | 2/2003 | Williams |
| 6,554,611 B2 | | 4/2003 | Chishti et al. |
| 6,602,070 B2 | * | 8/2003 | Miller et al. ........ 433/24 |

* cited by examiner

*Primary Examiner*—Ralph A. Lewis
(74) *Attorney, Agent, or Firm*—Andrew Mottes; Daniel Becker; Joseph R. Heffern

(57) ABSTRACT

Provided, among other things, is a system for progressive palatal expansion, the system comprising a series of incremental expanders, including: a) a first incremental expander having a geometry selected to incrementally expand the palate; b) one or more intermediate expanders having geometries selected to progressively expand the palate; and, c) a final expander, having a geometry selected to expand the palate to a target desired breadth.

39 Claims, 3 Drawing Sheets

SYSTEM AND METHOD FOR PALATAL EXPANSION

The present invention relates to a system and method for progressively expanding the palate of a patient.

A variety of orthodontic problems are linked with a narrow palate. In certain circumstances the maxilla the size to accommodate the upper teeth. In other cases there is room for the upper teeth but the palate is so narrow that speech is impaired or made difficult. In other cases the palate is so high that it cuts down on the amount of air that can pass though the nose, so that deep breathing, without opening the mouth, is almost impossible. In all of these cases, palate expansion, that is separating and spreading the maxilla, may be helpful.

The palatal expansion device which is most commonly used in the prior art is affixed to the upper posterior molars usually with cement. A screw or other mechanism is employed to deliver a horizontal stretching force to the molars to stretch the palatal cartilage. In many cases a large horizontal force is delivered by the orthodontist upon placement. This can cause extreme discomfort including headaches, nasal discomfort and pain. In other cases the screw or other mechanism is employed incrementally one or more times a day. While this incremental approach eases some of the discomfort such devices, the incidence of discomfort remains high. Moreover, the devices are awkward and bulky, largely due to the mechanism. This bulkiness can cause difficulty with speech, swallowing and breathing. The screw or other mechanism can be difficult to operate and often involves use of a key which can be accidentally lost or swallowed. In addition these devices tend to accumulate plaque.

Other problems encountered are that prior art devices tend to tilt the teeth buccally (i.e., to angle toward the checks) rather than stretch the palate. Palatal expansion is most favorable if movement of the teeth that engage the expansion device is minimized in relative to the jaw (which is moved in the palatal expansion process).

The present system and method dramatically improves on prior art in that palatal expansion is performed without moving the device-engaged teeth in relation to the jaw, the expansion devices are not bulky and their presence does not significantly hamper speaking, swallowing and breathing. Further the expansion devices can readily be constructed of materials that do not harbor, or minimally harbor, plaque and bacteria. Such resistance to plaque and bacteria provides a decreased likelihood of irritation of gums or palate when compared with other similar devices. Additionally, each incremental delivery of horizontal stretching force to the mid-palatal cartilage is delivered over, for example, twenty four hours to one week. By providing the patient with pre-formed expansion devices that the patient can apply when appropriate, it is more practical to ease the amount of expansion pressure that must be applied with each adjustment.

SUMMARY OF THE INVENTION

Provided is a system for progressive palatal expansion, the system comprising a series of incremental expanders including a first incremental expander having a geometry selected to expand the palate, one or more intermediate expanders having geometries selected to progressively expand the palate and a final expander, having a geometry selected to expand the palate to a target desired breadth. The expanders can comprise pre-formed devices having a first molar-engaging region adapted to engage upper molars on a first side of the upper jaw, a second molar-engaging region adapted to engage upper molars on a second side of the upper jaw and palatal region with a geometry selected to fit against the shape of the palate while providing pressure to incrementally expand the palate In a preferred embodiment, each of the expanders in the series of expanders comprises two molar regions, one on each side, each with one or more cavities, each cavity being adapted to fit over one of the patient's molars. In an especially preferred embodiment each molar region comprises two cavities, such that each molar region fits over two posterior molars or premolars. Each expander further comprises a palatal region, which separates the two molar regions and fits against the patient's palate. The distance between the molar regions in the series of expanders is sequentially greater. Each of the expanders can be pre-fitted to a given patient's upper jaw and each expander is fitted to engage molars such that the molars maintain the same relative orientation to the upper jaw.

The palatal region of the device is believed to primarily harbor the energy used to stretch the midpalatal region. It will be recognized by those of skill that energy enhancing features can be placed in this region, such as springs and thermally active materials such as metals designed to expand over time at body temperature. Such material can be used to reduce the number of expanders needed to achieve a target palatal expansion. Preferably, the distance between the molar regions of one expander differs from the distance between the molar regions of the prior expander by not more than 2 mm.

In preferred embodiments the expanders are formed out of a polymer or a metal such as flexible nickel titanium, or copper nickel titanium.

A method of expanding the palate of a patient is also described. The method comprises positioning each expander in a series of expanders in position to expand the palate, leaving the expander in position for a period of time and replacing the expander with the next expander in the series until the desired palatal expansion has occurred. For example, the method can comprise: a) generating from an initial physical or electronic model of the patient's upper jaw a series of incremental expanders, including: i) a first incremental expander having a geometry selected to incrementally expand the palate; ii) one or more intermediate expanders having geometries selected to progressively expand the palate; and, iii) a final expander, having a geometry selected to expand the palate to a target desired breadth; and b) sequentially engaging the expanders with the patient's upper jaw, each for a period of time effective to expand the palate, over the course of treatment, to approximately the target desired breadth.

In a preferred embodiment all expanders are produced before the first expander is positioned.

DETAILED DESCRIPTION OF THE INVENTION

The system of the present invention comprises a series of incremental expanders adapted to fit over the molars of a patient and expand the palate. The series of incremental expanders includes a first incremental expander having a geometry selected to expand the palate, one or more intermediate expanders having geometries selected to progressively expand the palate and a final expander, having a geometry selected to expand the palate to a desired target breadth, which can be the ultimate breadth desired to be achieved by a course of treatment, or an intermediate target.

Figure 1:
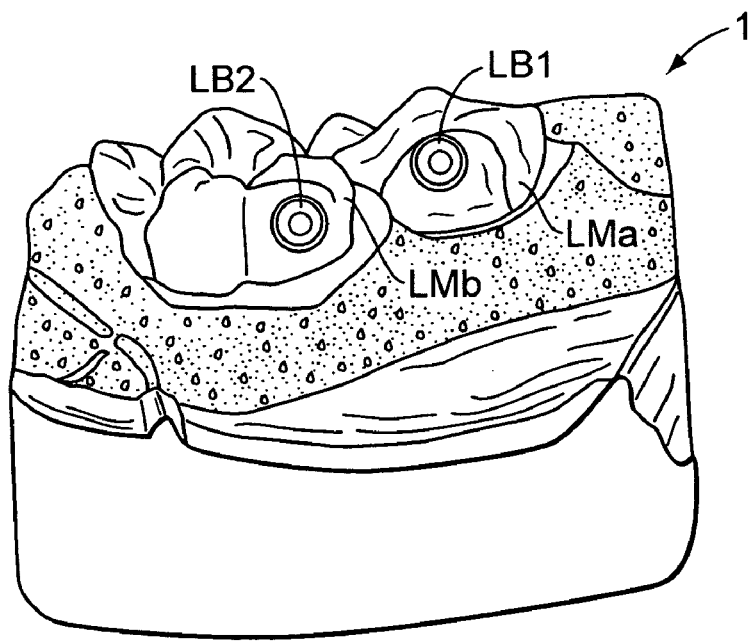
FIG. 1 displays a model of a patient's upper jaw with moldings in place.
Figure 2:
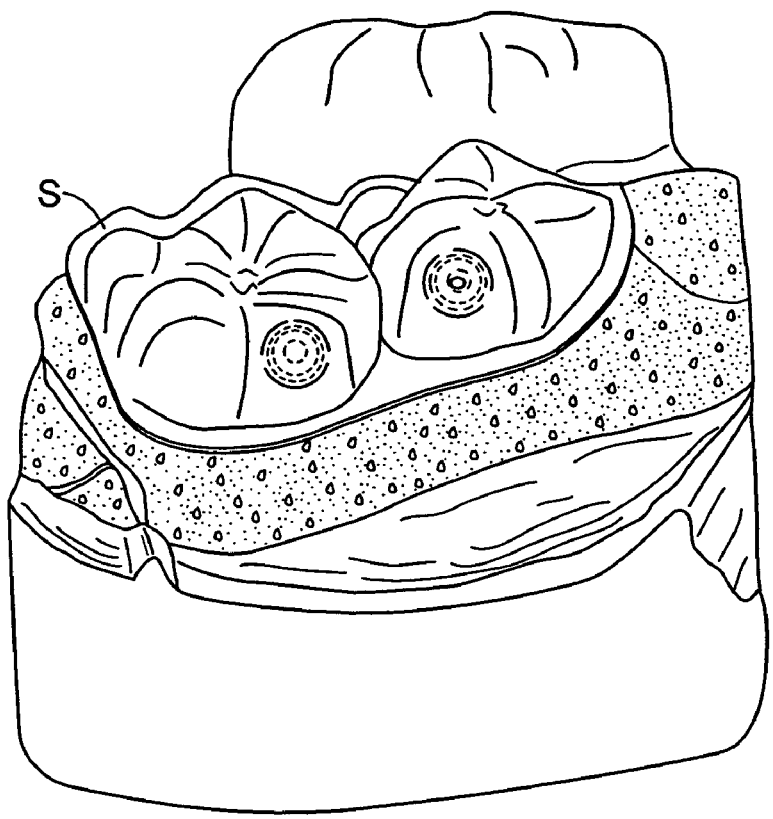
FIG. 2 displays the upper jaw model of FIG. 1 with a template for forming moldings on a patient's molars in place.

The invention can be described with reference to the illustrative drawings. In FIG. 1, a model 1 of the patient's upper jaw and palate, in this case an epoxy model, has cemented to it moldings (e.g., in this case, bowl-shaped, 3 mm diameter, 1.5 mm depth, 0.75 mm concavity). Shown on the buccal (cheek) side of second primary molar LMa and first permanent molar LMb of the left side of the model 1 are moldings LB1 and LB2, respectively. Not shown in the drawing are corresponding bowl shaped moldings for the right side of the model 1. The moldings are optional though preferred, as is the use of two such moldings per side. The model with moldings can be used to form a template 5, for example a polymeric (acrylic, such as from Type A acrylic sheets of 0.040 gauge thickness from Raintree Essix Company, Metairie, La.), as shown in FIG. 2. Where appropriate acrylic materials are used, the template can be cured by appropriate heating (e.g., for 45 seconds).

The template 5 can be used to place moldings onto the patient's molars. The moldings can be formed, for example, of light curable composite, such as the Cabrio™ composite available from Discuss Dental (Culver City, Calif.). The patient's molars can be prepared by, for example, a prophylaxis cleaning with moistened pumice, and a slow speed dental hand piece with a prophy cup to remove plaque and debris. The teeth can then, for example, be rinsed with a 37% phosphoric acid gel for 15 seconds, rinsed and dried thoroughly until the enamel appears frosted. The etched surfaces are then, for example, primed with a light-sensitive composite material primer, such as Cabrio™ primer (Discuss Dental). Then the template 1 is loaded with composite at the molding negatives to fill the areas where the moldings are to be placed and the template is placed in the patients' mouth. The material is then light cured using a visible light curing light such as the Optilux 501™ light source (Kerr Dentistry, Orange, Calif.), for 30 seconds per molding. After the template is removed from the molars, excess composite material can be trimmed from the molars with a dental hand piece. The moldings can be placed so that 1.5 mm or more of enamel exists gingival to the molding (between the molding and the gums).

Figure 3:
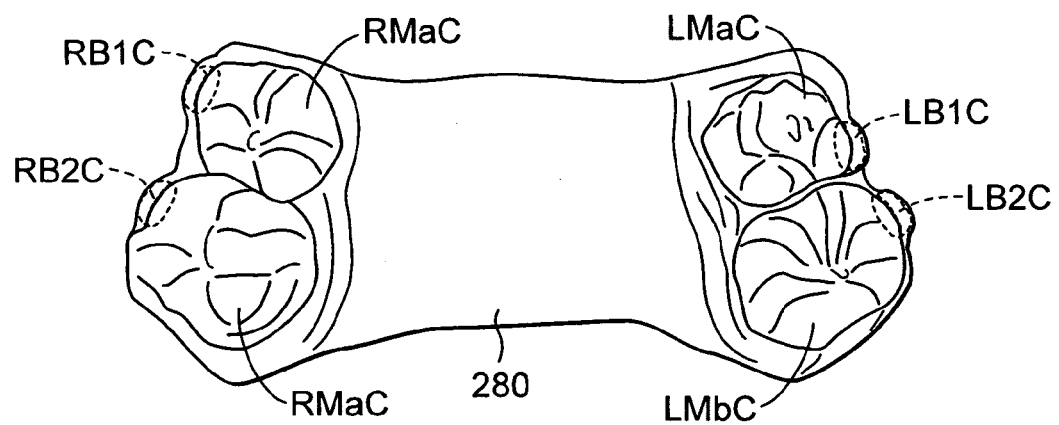
FIG. 3 displays a bottom view (from the perspective of a patient's mouth) of an expander.
Figure 4:
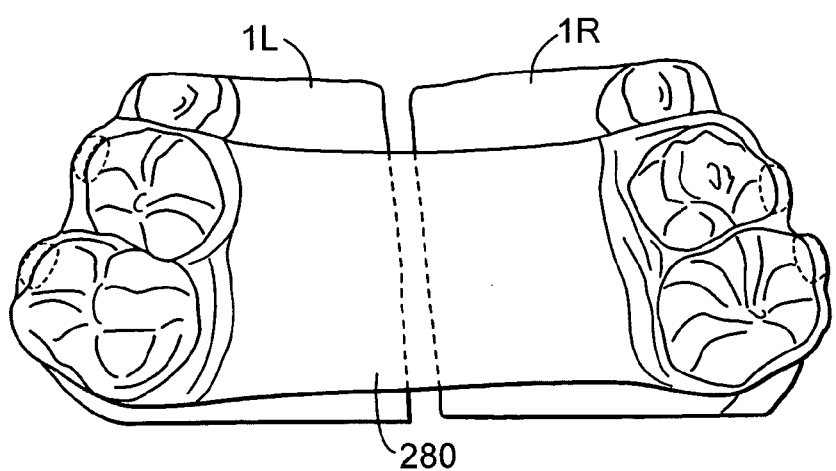
FIG. 4 displays a bottom view of the expander of FIG. 3 fitted to an upper jaw model for which the left and right sides have been cut into separate pieces.
Figure 5:
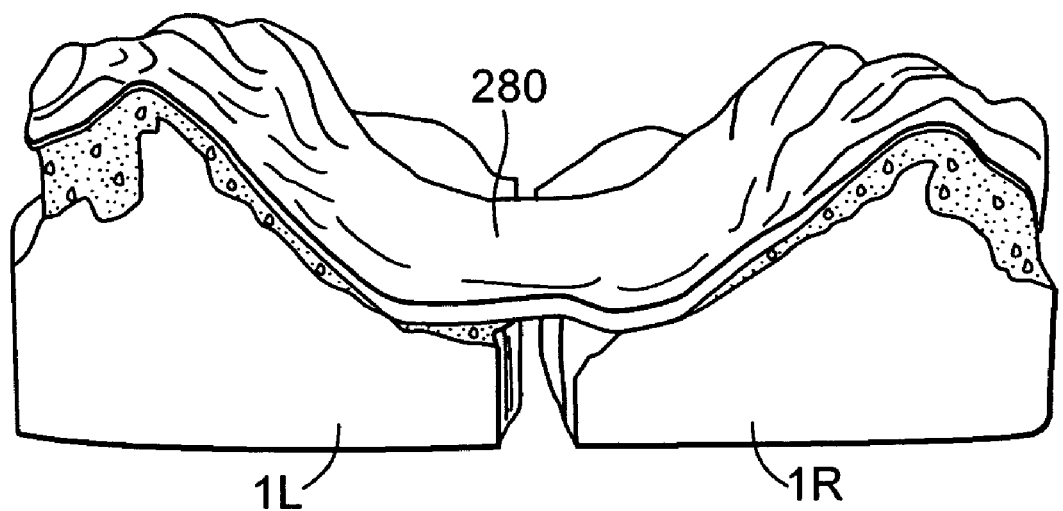
FIG. 5 shows a rear view of the expander of FIG. 3 fitted to the separated upper jaw model.

FIG. 4 shows the upper jaw model separated into a left portion 1L and a right portion 1R. The separated halves are used to form expander 280, which in this illustration is the 28th and final expander in a series. To form the intermediate expanders, the two halves are serially separated further from their initial relationship, and expanders are made for each anticipated separation distance. FIG. 3 shows expander 280 separated from the model. Expander 280 has two cavities RMaC, RMbC, for engaging molars on the right side, and two cavities LMaC, LMbC, for engaging molars on the left side. These cavities are seen as their outward projection on the bottom of the expander. The molar-engaging cavities themselves have cavities for engaging the moldings, namely molding-engaging cavities RB1C, RB2C, LB1C, LB2C. FIG. 5 is a rear view of expander 280.

The incremental expanders of the present invention are preferably produced before beginning the expansion of the patient's palate. In a preferred embodiment there are more than 2 intermediate expanders. In a more preferred embodiment there are more than 10 and in an especially preferred embodiment there are more than 20 intermediate expanders in the series.

An impression of the patient's upper teeth and jaw is taken using a molding material such as polyvinylsiloxane (PVS) or wax. A model of a patient's upper jaw, formed, for example, from epoxy, is generated from the impression. The model can be used as described below to provide a pre-fitted system for progressive palatal expansion.

Material for moldings can be, for example, placed onto the buccal (cheek side) surfaces on both sides of the upper jaw model's two posterior molars. A positive pressure thermal forming machine is used to form a template for placing correspondingly located moldings on the patient's molars. (The description herein of moldings should not suggest that these moldings are necessarily bowl-shaped, though this is a convenient shape. Those of skill will recognize that a number of shapes can be used to serve the function of securing the positioning of expanders and reducing outward pressure on the molars, thereby limiting buccal tipping of the molars.) The template material, where thermally curable, is heated and thermally formed over the epoxy model including the maxillary (upper jaw) teeth with the moldings and the palate. In a preferred embodiment the sheet is 0.040 gauge in thickness and is heated for approximately 45 seconds before forming. The template is removed from the epoxy model and trimmed so that it engages, in a preferred embodiment, only molar teeth, and retains an appropriate portion bridging between the molar-engaging portions. In a more preferred embodiment the template engages two molar teeth on each side.

Moldings, such as those shown in FIGS. 1 and 2 affixed to a jaw model, are, in a preferred embodiment, affixed to the patient's molars using the template. The moldings are preferably made of acrylic, ceramic or metal, with dimensions of approximately 3 mm in diameter and 1.5 mm in depth with a concavity of 0.75 mm at the deepest central position (from the reverse image perspective of the corresponding cavities in the template). These moldings are preferably cemented onto the model using super glue. Prior to placement of the moldings on the patient's molars, the patient's molars preferably receive a prophylaxis cleaning.

Alternatively, the moldings can be placed first onto the buccal aspect of the patient's molars (or premolars) on each side (preferably the two most posterior), and then the impression used to make the upper jaw model can be taken over the teeth, including the bowl shaped moldings. Or, the molars can be conditioned chemically, or mechanically to limit or prevent tipping of the involved molar or premolar teeth. Alternatively, the moldings can be affixed by other methods recognized in the art. For example, the moldings can be sculpted by hand, first bonding the light sensitive composite material to the molars, and then using a dental hand piece to sculpt the appropriate dimensions. Or, ceramic or metal retentive moldings can be attached to serve the same anti-tip function through a cementing, or bonding process.

Other methods of forming the template are known in the art. These methods include but are not limited to use of an intra-oral 3D scanner to generate the template from the patients upper teeth or, to scan the PVS impression for use with computer controlled sculpting devices used to form the templates.

In one method of producing the series of expanders of the present invention the upper jaw model is separated into parts (preferably halves) using, for example, a dental lab saw. The resulting two sections are serially separated at successively larger distances to provide the model for the respective expander. To facilitate the process, the two upper jaw model pieces can be secured to a device having a mechanical or electromechanical mechanism for separating the two pieces in a manner accurate to, for example, provide for approximately 0.5 or approximately 0.25 mm steps, or to provide for steps from 0.1 to 0.25 mm.

Filler material may be placed between the two halves of the model in order to ensure that the two halves remain aligned. A material, such as Triad Gel™ (available from Raintree Essix Company, Metairie, La.), which does not melt or distort when the expanders are thermal formed onto the epoxy model, is preferred for this purpose. The two halves of the model are moved sequentially further apart such that the inter-molar distance is adjusted by a defined amount for each new expander in the series. The inter-molar distance can be measured using a clear plastic millimeter ruler or other measuring device. The distance may be measured from the juncture of the lingual groove of the most posterior molar to the same tooth on the opposite side at the gumline. Such movement preferably occurs at the mid-palatal region sagittally (at the modeled suture between the palatal bones of the maxilla).

The first expander is thermal formed using methods known in the art. In a preferred embodiment a sheet of polymer is heated and thermal formed over the upper jaw model, including the appropriate molars and, if present, the moldings. The template is removed from the upper jaw model and trimmed so that it includes, in a preferred embodiment, only molar teeth, (with a negative of the moldings), and the portion of the palate between the molars. In a more preferred embodiment the template includes two posterior molar teeth on each side.

The palatal region of the expander can be reinforced while the expander is still attached to the upper jaw model. A preferred method is the application of chemically cured methyl methacrylate, which is preferably applied using powder and liquid polymer-forming material. Approximately 3 mm of acrylic material in sheet form may be added to the thermally formed plastic. Such reinforcement is one method of increasing the pressure that effects palatal expansion.

The model is placed in hot water (e.g., 100° F.) for curing for approximately 10 minutes. The cured expander is removed from the epoxy model, and may be trimmed. Trimming is preferably performed using a lab hand piece with an acrylic bur. The acrylic portion may be polished with pumice, and, if desired, a fine shine can be added.

The same process is utilized to generate each expander in the series, the distance between the molar regions of the expander progressively increasing until the desired palatal width is reached. In preferred embodiments the distance between the molar regions of the expanders increases regularly throughout the series of expanders. In one preferred embodiment each expander is less than 2 mm wider than the expander before it in the series. In a more preferred embodiment each expander is 0.5 mm wider than the expander before it in the series. In another preferred embodiment each expander is 0.25 mm wider than the expander before it in the series.

Palatal expansion is generated by regular replacement of the first expander in the series with intermediate expanders until the final expander is reached. In a preferred embodiment there are at least two intermediate expanders and in a more preferred embodiment there are at least ten intermediate expanders. The expanders in the series are progressively wider such that when the final expander is positioned and utilized the patient's palate has been widened a target distance. In one preferred embodiment the expanders are switched at regular periods between approximately 24 hours and approximately 1 week. In a more preferred embodiment the expanders are replaced every 48 hours or every 24 hours. The expanders are preferably left in throughout the period. After removal of each progressive expander, the patient should thoroughly brush and floss, and then presses on the next expander.

If the next expander in the series does not insert with good adaptation on the teeth and palate, more time may be needed to effect true growth and reduce molar buccal tipping. The patient can be advised to use the present expander for another period of time if this occurs. After good adaptation occurs, the next expander is placed.

After a desired amount of expansion is achieved, the final expander can be used to retain the affected palatal expansion. Or, braces can be added to the patients' teeth, and an orthodontic archwire used to hold the expansion. A variety of alternative cross palatal appliances can be used to hold the expansion, such as a trans-palatal bar, a nance, or a Hawley™ retainer.

Typically the younger the patient, the more flexible the palate, as the amount of mid palatal cartilage is greater at a younger age. 0.25 mm per day of expansion has worked extremely well for 6 and 7 year old patients. This rate can be effective for older patients, such as 8, 9 or 10 year olds, or spacing smaller increments or larger timing increments can be used. Expander exchanges can be done at, for example, 1 week intervals for patient's that adapt slowly.

Where the expanders otherwise adequately engage the molars, or where other techniques are used to inhibit buccal tipping, the moldings may not be needed. For example, the progressive expansion system can be used in combination with conventional braces, in which case the moldings may not be needed. Braces can be used in combination with the system of plastic incremental expanders on the buccal surfaces or on the lingual surfaces of the teeth to limit or prevent tipping of the molars. Alternately wires and added acrylic can be incorporated to affect anti-tipping on the upper molars, and to assist in true growth of the maxilla.

Materials other than thermal formed plastic can be used to form the series of expanders. These materials include, but are not limited to metals such as flexible nickel titanium, or copper nickel titanium and can be used in combination with the buccal moldings, or without them, and also in combination with braces to achieve palatal expansion.

What is claimed:

1. A system for progressive palatal expansion, the system comprising a series of incremental expanders, including: a) a first incremental expander having a geometry selected to incrementally expand the palate; b) one or more intermediate expanders having geometries selected to progressively expand the palate; and, c) a final expander, having a geometry selected to expand the palate to a target desired breadth.

2. The system of claim 1, wherein each of the expanders is pre-fitted to a given patient's upper jaw and each expander is fitted to engage molars such that movement of the molars in relative orientation to the upper jaw is minimized.

3. The system of claim 1, wherein each of the expanders comprises: a) two molar regions, the molar regions each having one or more cavities, each cavity adapted to fit over one of the patient's molars; and, b) a palatal region, the palatal region separating the two molar regions and fitting against the patient's palate, the distance between the molar regions in the series of expanders being sequentially greater.

4. The system of claim 3, wherein each expander is formed out of polymer.

5. The system of claim 3, wherein the distance between the molar regions of one expander differs from the distance between the molar regions of the prior expander by not more than 2 mm.

6. The system of claim 5 wherein the distance between the molar regions of one expander differs from the distance between the molar regions of the prior expander by approximately 0.5 mm.

7. The system of claim 5 wherein the distance between the molar regions of one expander differs from the distance between the molar regions of the prior expander by approximately 0.25 mm.

8. The system of claim 3, wherein each molar region comprises two cavities, such that each molar region fits over two posterior molars.

9. The system of claim 3, wherein the palatal region of each expander has a geometry selected to expand the palate by concentrating horizontal stretching force on the mid-palatal connective tissue, while minimizing force exerted against the teeth by each expander's molar regions that could lead to undesirable tooth movement of the device-engaged teeth relative to the maxilla.

10. The system of claim 3, wherein the palatal region of each expander has a thickness of at least 3 mm at its thickest point and the molar regions have a thickness of less than 3 mm.

11. The system of claim 1, wherein there are at least 2 intermediate expanders.

12. The system of claim 1, wherein there are at least 10 intermediate expanders.

13. The system of claim 1, wherein there are at least 20 intermediate expanders.

14. A method of expanding the palate of a patient using the system of claim 1, the method comprising positioning each expander in the series of expanders in position to expand the palate of the patient, leaving the expander in position for a period of time and replacing the expander with the next in the series until the desired palatal expansion has occurred.

15. The method of claim 14, wherein the period of time is between approximately 24 hours and approximately 1 week.

16. The method of claim 14, wherein each of the expanders comprises: a) two molar regions, the molar regions each having one or more cavities, each cavity adapted to fit over one of the patient's molars; and, b) a palatal region, the palatal region separating the two molar regions and fitting against the patient's palate, the distance between the molar regions in the series of expanders being sequentially greater.

17. The method of claim 16, wherein the distance between the molar regions of one expander differs from the distance between the molar regions of the prior expander by not more than 2 mm.

18. The method of claim 17, wherein the distance between the molar regions of one expander differs from the distance between the molar regions of the prior expander by approximately 0.5 mm.

19. The method of claim 18, wherein the distance between the molar regions of one expander differs from the distance between the molar regions of the prior expander by approximately 0.25 mm.

20. The method of claim 17, wherein the distance between the molar regions of one expander differs from the distance between the molar regions of the prior expander by from 0.1 mm to 0.2 mm.

21. The method of claim 16, wherein all expanders are produced before the first expander is positioned.

22. The method of claim 16, wherein the palatal region of each expander has a geometry selected to expand the palate by concentrating horizontal stretching force on the mid-palatal connective tissue, while minimizing force exerted against the teeth by each expander's molar regions that could lead to undesirable tooth movement of the device-engaged teeth relative to the maxilla.

23. The method of claim 16, wherein the palatal region of each expander has a thickness of at least 3 mm at its thickest point and the molar regions have a thickness of less than 3mm.

24. The method of claim 14, wherein there are at least 2 intermediate expanders.

25. The method of claim 14, wherein there are at least 10 intermediate expanders.

26. The method of claim 14, wherein there are at least 20 intermediate expanders.

27. The method of claim 14, wherein all expanders are produced before the first expander is positioned.

28. A method of expanding the palate of a patient, the method comprising: a) generating from an initial physical or electronic model of the patient's upper jaw a series of incremental expanders, including: i) a first incremental expander having a geometry selected to incrementally expand the palate; ii) one or more intermediate expanders having geometries selected to progressively expand the palate; and, iii) a final expander, having a geometry selected to expand the palate to a target desired breadth; and b) sequentially engaging the expanders with the patient's upper jaw, each for a period of time effective, over the course of treatment, to expand the palate to approximately the target desired breadth.

29. The method of claim 28, wherein each of the expanders comprises: 1) two molar regions, the molar regions each having one or more cavities adapted to fit over one of the patient's molars; and, 2) a palatal region, the palatal region separating the two molar regions and fitting against the patient's palate, the distance between the molar regions in the series of expanders being sequentially greater.

30. The method of claim 29, further comprising affixing a molding to the buccal side of at least one of the patient's posterior molars on each side, wherein the molar region of the expanders further incorporates one or more cavities adapted to fit over each molding.

31. The method of claim 29, wherein each expander is formed out of polymer.

32. The method of claim 29, wherein the distance between the molar regions of one expander differs from the distance between the molar regions of the prior expander by not more than 2 mm.

33. The method of claim 32, wherein the distance between the molar regions of one expander differs from the distance between the molar regions of the prior expander by approximately 0.5 mm.

34. The method of claim 32, wherein the distance between the molar regions of one expander differs from the distance between the molar regions of the prior expander by approximately 0.25 mm.

35. The method of claim 29, further comprising positioning each expander in the series of expanders in position to expand the palate of the patient, leaving the expander in position for a period of time and replacing the expander with the next in the series until the desired palatal expansion has occurred.

36. The method of claim 35, wherein the period of time is between approximately 24 hours and approximately 1 week.

37. The method of claim 28, wherein there are at least 2 intermediate expanders.

38. The system of claim 28, wherein there are at least 10 intermediate expanders.

39. The system of claim 28, wherein there are at least 20 intermediate expanders.

* * * * *